United States Patent [19]

Stiso et al.

[11] 4,376,827

[45] Mar. 15, 1983

[54] COMPOSITION, TEST DEVICE AND METHOD FOR DETERMINING THE IONIC STRENGTH OR SPECIFIC GRAVITY OF A LIQUID SAMPLE UTILIZING A STRONG POLYELECTROLYTE

[75] Inventors: Sisto N. Stiso, Elkhart; Rodric H. White-Stevens, Howe, both of Ind.

[73] Assignee: Miles Laboratories, Inc., Elkhart, Ind.

[21] Appl. No.: 246,269

[22] Filed: Mar. 23, 1981

Related U.S. Application Data

[63] Continuation of Ser. No. 61,805, Jul. 30, 1979, abandoned.

[51] Int. Cl.$^3$ ............................................. G01N 9/36
[52] U.S. Cl. ......................................... 436/2; 436/169; 422/56; 422/57
[58] Field of Search ................. 23/230 R, 230 B, 924, 23/901, 908, 909, 910, 915; 422/56, 57; 73/32 R; 252/408; 210/662

[56] References Cited

U.S. PATENT DOCUMENTS

| | | |
|---|---|---|
| 3,282,650 | 11/1966 | Bannigan et al. . |
| 3,447,904 | 6/1969 | Rupe ................................ 252/408 |
| 3,449,080 | 6/1969 | Edwards .............................. 422/56 |
| 3,598,704 | 8/1971 | Dahlquist . |
| 3,728,226 | 4/1973 | Louderback ......................... 23/908 |
| 4,076,502 | 2/1978 | Dugle et al. ..................... 23/230 R |
| 4,092,115 | 5/1978 | Rupe et al. .......................... 252/408 |
| 4,318,709 | 3/1982 | Falb et al. ........................ 23/230 B |

*Primary Examiner*—William F. Smith
*Attorney, Agent, or Firm*—Edward H. Gorman, Jr.

[57] ABSTRACT

A composition is disclosed for determining the ionic strength or specific gravity of an aqueous test sample, the composition comprising a strongly acidic or strongly basic polyelectrolyte, a buffer substance capable of providing a pH of about 5.5, and an indicator means capable of producing a detectable response to ion exchange between the polyelectrolyte and the sample. The test device comprises a carrier matrix incorporated with the test composition, and the method for its use comprises contacting an aqueous test sample with the device and observing a detectable response.

22 Claims, 6 Drawing Figures

EFFECT OF SPECIFIC GRAVITY ON pH OF TEST DEVICES CONTAINING PSS AND BUFFERS.

EFFECT OF SPECIFIC GRAVITY ON pH OF TEST DEVICES CONTAINING PSS WITHOUT BUFFER.

EFFECT OF SPECIFIC GRAVITY ON pH OF TEST DEVICES CONTAINING PVS AND BUFFERS.

EFFECT OF SPECIFIC GRAVITY ON pH OF TEST DEVICES CONTAINING PVS WITHOUT BUFFER.

EFFECT OF SPECIFIC GRAVITY ON pH OF TEST DEVICES CONTAINING PVB WITHOUT BUFFER.

EFFECT OF SPECIFIC GRAVITY ON pH OF TEST DEVICES CONTAINING PVB AND BUFFERS.

COMPOSITION, TEST DEVICE AND METHOD FOR DETERMINING THE IONIC STRENGTH OR SPECIFIC GRAVITY OF A LIQUID SAMPLE UTILIZING A STRONG POLYELECTROLYTE

CROSS REFERENCES TO RELATED APPLICATIONS

The present application is a continuation of U.S. patent application Ser. No. 61,805 filed July 30, 1979 now abandoned.

BACKGROUND OF THE INVENTION

1. Field of the Invention

The present invention relates to the determination of the ionic strength or specific gravity of a test sample. More particularly, it relates to a composition, test device and method for determining the ionic strength or specific gravity of an aqueous test sample.

The determination of the specific gravity of a liquid has application in numerous arts. Thus, such unrelated disciplines as brewing, urinalysis, water purification, preparation of drinking water aboard a ship at sea, etc. all involve the measurement of specific gravity. Needless to say, a quick, facile method for determining this property would greatly enhance the state of many scientific arts, including any technology where rapid, accurate determination of specific gravity would be beneficial. Thus, for example, if a medical laboratory technician could accurately measure the specific gravity of a urine sample in a matter of seconds, not only would the rapid results aid the physician in diagnosis, but also laboratory efficiency would increase to a degree where many more analyses could be performed than were heretofore possible.

Although the present invention lends itself to a vast range of applications, for purposes of clarity this discussion will be couched largely in terms of the determination of the ionic strength or specific gravity of urine. Applications to other disciplines will become apparent from an understanding of how this invention relates to urinalysis.

The determination of urine specific gravity is of considerable value in the understanding and clinical management of electrolyte disturbances. Hence, complete urinalysis should, and usually does, include a specific gravity determination. Generally, such a determination would include the measurement of specific gravity directly with a suitable device, but equally useful is the measurement of some related property, such as osmolality or ionic strength, which can then be referred back to corresponding specific gravity values.

Specific gravity is a dimensionless term and relates, in the case of a solution, to the ratio of the weight of a certain volume of the solution to that of an equal volume of water at the same temperature. For solutions, such as urine, specific gravity is related to the number, density, ionic charge, and weight of the various species of dissolved solutes.

2. Description of the Prior Art

Prior art methods for determining specific gravity utilize hydrometers, urinometers, pycnometers, gravimeters, refractometers, and the like. Although these prior art procedures are satisfactorily sensitive in most cases, they all involve fragile, bulky instruments which must be constantly cleaned, maintained, and calibrated in order to continuously assure their reliability. In addition, there are many inconveniences associated with the mechanics of using these instruments. There may be a difficulty in reading the meniscus. Froth or bubbles on the liquid surface may interfere with the reading. There is a tendency for urinometers to adhere to the sides of the vessel containing the liquid sample. In the case of urine, the sample quantity is frequently inadequate for accommodating one of the aforementioned devices.

A recent breakthrough in which all of the above disadvantages have been virtually eliminated, and which affords rapid osmolality (ergo, specific gravity) determination, is disclosed in U.S. Pat. No. 4,015,462, assigned to the present assignee. This patent describes an invention in which a carrier matrix is incorporated with osmotically fragile microcapsules, the walls of which are composed of a semi-permeable membrane material. Encapsulated inside the walls is a solution containing a coloring substance. When the capsules are in contact with a solution having a lower osmolality than that within the capsules, an osmotic gradient occurs across the capsule walls in the direction of the lower osmolality, thereby increasing the hydrostatic pressure within the capsules, thus causing them to swell and, ultimately, to rupture, releasing their colored contents. The amount of color formed from this phenomenon is a function of the specific gravity of the solution.

It can be seen from the foregoing that besides the numerous devices which measure specific gravity directly, it is also possible to measure specific gravity using an indirect means such as the osmolality of a solution. Yet another way of estimating specific gravity without measuring it directly involves a determination which is proportional to the ionic strength of a solution. Such an approach is utilized by the present invention. It is well known that the specific gravity of an aqueous system is greatly affected by the presence of charged species. Thus, in the case of ionic solutions, it is possible to closely approximate the specific gravity of the respective solutions via measurements proportional to their ionic strengths and referring those measurements to a precalibrated reference system.

The term "ionic strength" refers to the mathematical relationship between the number of different kinds of ionic species in a particular solution and their respective charges. Thus, ionic strength $\mu$ is represented mathematically by the formula $$\mu = 1/2 \Sigma c_i z_i^2$$

in which c is the molal concentration of a particular ionic species and z the absolute value of its charge. The sum $\Sigma$ is taken over all the different kinds of ions (i) in solution.

U.S. Pat. No. 3,449,080 discusses measuring dissolved sodium or chloride ions. It is directed to a test device for determining the concentrations of these ions in body sweat. Briefly, there is disclosed in this patent the use of ion exchange resins together with a pH indicator. Using this device, the presence of sodium or chloride ions is said to be determined through a color change resulting from interaction between the ion exchange resin and the pH indicator. Whereas this reference purports to disclose a way of measuring ionic strength, it was found by the present inventors that such teachings, as set forth in the examples, were inapplicable to the measurement of specific gravity.

Both the osmolality and ionic strength approaches to indirectly determining specific gravity could conceivably be affected insofar as accuracy is concerned by the presence of nonionic species. Accordingly, U.S. Pat. No. 4,108,727, assigned to the present assignee, is directed to a method for removing this potential source of inaccuracy, and discloses a device in which the specific gravity-sensitive system contains an ionizing agent capable of converting the non-ionic solute to ionized species.

Finally, U.S. patent application No. 958,630, filed Nov. 8, 1978, and assigned to the present assignee, describes a device for using ionic strength for measuring specific gravity. This device utilizes a partially neutralized weak polyelectrolyte in the presence of a pH indicator. The present invention, on the other hand, represents a new approach whereby different polyelectrolytes having different properties are used.

To summarize the present state of the art as it might pertain to the present invention, many methods are known for the measurement of specific gravity, both direct and indirect. Direct measurement includes utilizing devices which are fragile, bulky and expensive, and which must be constantly cleaned, maintained and calibrated. Of the indirect methods, the measurement of the colligative solution property known as osmolality can provide an accurate correlation to specific gravity. The present invention utilizes a different perspective, the relationship between specific gravity and the ionic strength of a solution, and provides a device, composition and method for taking advantage of this relationship. As indicated above, U.S. Pat. No. 3,449,080 describes a method of gauging the concentration of sodium and/or chloride ions in body sweat. This patent utilizes the affinity of weakly acidic or weakly basic ion exchange resins for the unknown ions, and the color changing capacity of known pH indicators. None of the prior art known to the present inventors at the time of filing of the instant application teaches or suggests the invention presently disclosed and claimed.

SUMMARY OF THE INVENTION

Briefly, the present invention relates to a test composition, device, and method for determining the specific gravity of an aqueous test sample. The composition comprises a strongly acidic or basic polyelectrolyte polymer, a buffer capable of providing a pH of at least about 5.5, and an indicator means capable of producing a detectable response to ion exchange in the range of pH provided by the buffer. The device of the present invention comprises a carrier matrix incorporated with the composition. The method of the present invention comprises contacting a test sample with the device or composition and observing a detectable response, such as a color change.

BRIEF DESCRIPTION OF THE DRAWINGS

FIGS. 1, 3 and 5 show the capacity of various embodiments of the present invention for determining specific gravity in urine.

FIGS. 2, 4 and 6 demonstrate the importance of including the presently claimed buffers in the composition. All six graphs represent the relationship of pH change as effected by urines of varying specific gravities.

DETAILED DESCRIPTION OF THE INVENTION

Figure 1:
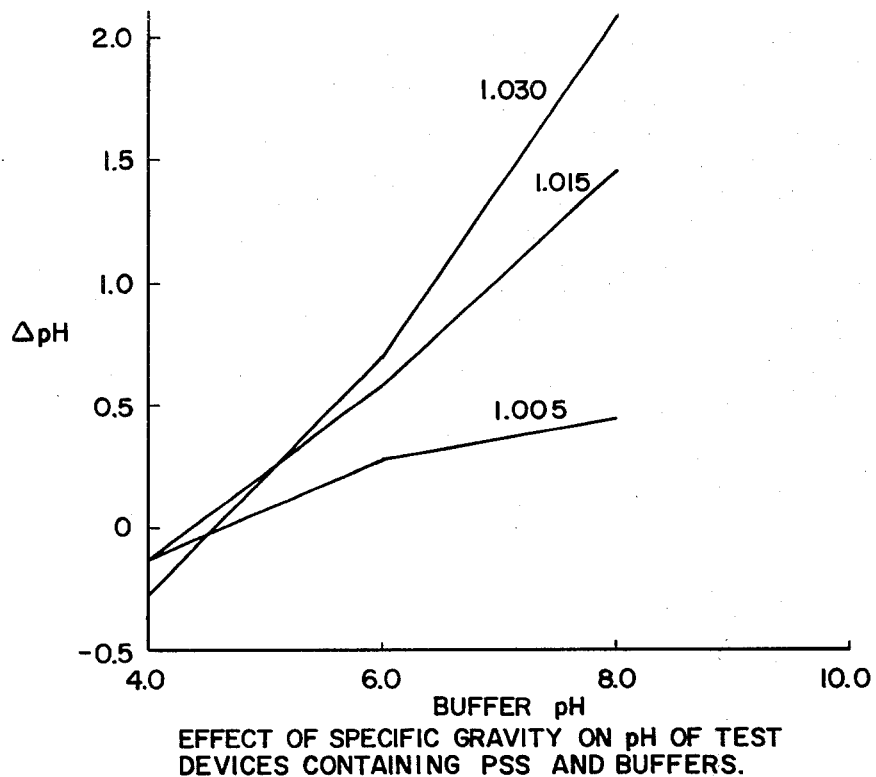
FIGS. 1-6 are graphic portrayals of data derived from experiments set forth, infra, in the Examples.

The presently claimed composition comprises, as one ingredient, a strongly acidic or basic polyelectrolyte. Numerous examples of such polymers are known in the art, their common characteristics centering about the degree of dissociation of the ionic pendant groups when the polymer is subjected to an aqueous environment. Most polyelectrolytes are soluble or partially soluble in water, and are readily ionizable, depending on the ionic nature of (a) the aqueous system and (b) the ionizable species on the polymer chain.

Thus a polyelectrolyte is branded weakly or strongly acidic or basic depending on its ionic behavior. Generally, a polyelectrolyte which nearly completely ionizes when contacted with water, such as poly(vinylsulfuric acid), poly(styrene sulfonic acid), and poly(vinylbenzyl trimethylammonium chloride) are considered strong polyelectrolytes. Weak polyelectrolytes, on the other hand, contain weakly acidic or basic ionizable groups. The charge density along the molecular chain of these polymers can be varied by varying the degree of neutralization, whereas the transition between the fully ionized and nonionized states is fleeting in strong polyelectrolytes. Examples of weakly acidic or weakly basic polyelectrolytes are poly(acrylic acid) and poly(4-vinylpyridine), respectively.

The composition of the present invention includes strongly basic or acidic polyelectrolytes, but more particularly it includes the presence of a suitable buffer and a pH indicator means capable of producing a detectable response to a relatively small change in pH in the range of the buffer. Thus, if the buffer selected provides a pH of about 6, the indicator must be capable of producing a response to pH changes near pH 6.

In general the present invention must be designed around the anticipated test sample. This is achieved by predicting the test sample pH range as closely as possible and choosing a buffer system which will approximate the sample pH. This approach to choosing the proper buffer reduces the possibility of test interference from the buffering capacity of the test sample itself. Thus in the case where urine is the anticipated test sample whose specific gravity is to be determined, a buffer system should be chosen to yield a pH of about 6 to about 8.

Moreover, it has been found that regardless of the pH of the test sample, the present system permits optimum resolution of ionic strength at a pH of 5.5 or greater. With urine and NaCl solutions, which exhibit pH values of about 6.5 and 7.0, respectively, it was necessary to provide a buffer capable of producing a pH of more than about 5.5. As buffers of higher pH were experimented with, with either strongly acidic or strongly basic polymers, it was found that greater sensitivity occurred with greater pH values. Thus, the sensitivities of poly(styrene sulfonic acid), poly(vinylsulfuric acid), and poly(vinylbenzyl trimethylammonium chloride) systems were markedly improved as the various buffers explored became more basic. This phenomenon will be discussed more fully in the Examples, infra.

Suitable buffers for use in the present invention include citrate salts (pH of about 5), phosphate salts (pH of about 5 to about 7), glycylglycine (pH of about 8), tris(hydroxymethylamino) methane (pH of about 8), and sodium bicarbonate (pH of about 10).

The term "pH indicator means" as used herein encompasses any suitable system capable of indicating a change in pH in the range of the particular buffer employed. It includes pH indicator compounds and mixtures thereof, pH meters, and other means determinable by a person having reasonable skill in the art, given the present disclosure. Thus a pH meter can be used with a standard pH electrode (in solution systems) or with a surface pH electrode (where the composition is incorporated with a carrier matrix). The pH meter response can then be observed over various ionic strength values and a reference system can be established, a particular change in pH corresponding to a particular test sample ionic strength.

Alternatively, known pH-sensitive chromogenic reagent compounds can be employed, and these can provide a change in or appearance of color, observable by the person performing the measurement, which is indicative of the ionic strength or specific gravity of the system being tested. If a chromogen is used, a reference color system can be established beforehand, so that a quick visual comparison of the composition and the reference system provides the sought after results. Examples of chromogens suitable for use in the present invention are bromthymol blue, alizarin, bromcresol purple, phenol red and neutral red; bromthymol blue having been found to be especially suitable.

The present invention includes a device in which a carrier matrix is incorporated with the presently disclosed test composition to provide a tool for obtaining rapid, reliable estimations of solution specific gravities. The carrier matrix is usually, but not necessarily, a porous substance such as filter paper. Other art-recognized forms of carrier matrix materials are felt, porous ceramic strips, and woven or matted glass fibers (U.S. Pat. No. 3,846,247). Also suggested are the use of wood, cloth, sponge material and argillaceous substances (U.S. Pat. No. 3,552,928). All such carrier matrix materials are feasible for use in the present invention, as are others such as polystyrene film. It has been found that filter paper is especially suitable.

In a preferred embodiment, filter paper is immersed in an aqueous solution of the polyelectrolyte, buffer and a chromogenic pH indicator and subsequently dried, thus forming a carrier matrix incorporated with the composition of the present invention.

The dried, reagent-bearing carrier matrix can be mounted on a backing material if desired. The test device, in a preferred embodiment, thus comprises a filter paper carrier matrix, incorporated with a strong polyelectrolyte, buffer and indicator means as described supra, the matrix being affixed to one side to an elongated piece of transparent polystyrene film. The matrix is secured to one end of the film by any suitable means, such as double-faced adhesive tape (e.g., Double Stick ® available from 3M Company), the other end of the polystyrene film serving as a handle. In use, such a device is held by the free end of the polystyrene film backing material, and the matrix end is immersed into the test sample (e.g., urine) and quickly removed. Any color formation or other detectable response is observed after a predetermined time and compared with a reference standard corresponding to responses to known solution ionic strengths or specific gravities.

Where a test device comprising a carrier matrix containing the composition is employed, a reference standard can comprise a series of color blocks depicting the color developed by the carrier matrix after a predetermined time in response to solutions of known ionic strengths. When testing an unknown sample, the carrier matrix of a test device is immersed in the sample, removed, and observed for the appearance of or change in color after the predetermined time. Any color response is then compared with the reference standard color blocks to ascertain the ionic strength or specific gravity of the sample.

The following Examples are provided to further teach how to make and use the present invention. Thus, preferred embodiments are described and analyzed. The Examples are meant to be illustrative only, and are in no way intended as limiting the scope of the invention described and claimed herein.

Example I—Test Devices Utilizing Poly(sytrenesulfonic acid)

A series of experiments was performed whereby a presently claimed composition and device were prepared, and their use in differentiating between various urine specific gravity levels was observed. The devices comprise paper carrier matrices impregnated with poly(styrenesulfonic acid) (hereafter PSS) obtained from Polysciences, Inc. of Warrington, Pa. as the strong polyelectrolyte, and a buffer. Strips were prepared using buffers providing pH values of 4.0, 6.0 and 8.0, respectively, and were tested using lyophilized urine solutions at various specific gravities. The pH indicator means employed was a pH meter having a flat surface electrode (obtained from Markson Science, Inc., No. 1207 BactiMedia combination pH/reference electrode).

The devices were prepared by saturating a piece of Eaton and Dikeman 204 filter paper with a solution of PSS in the respective aqueous buffer, and subsequently drying. The buffered solutions each contained 2% (grams per 100 ml.) PSS. The first buffer solution contained 0.05 M sodium citrate (pH=4.0), the second 0.05 M phosphate (pH=6.0) and the last 0.05 M glycylglycine (pH=8.0).

The strips prepared from each of the buffer solutions of PSS were compared by dipping into reconstituted urine solutions prepared from lyophilized urine, specifically TEK-CHEK ® available from the Ames Division of Miles Laboratories, Inc. The test solutions had specific gravities of 1.030, 1.015 and 1.005. A separate device was dipped in each test solution and the pH was measured using the flat electrode pH meter as the pH indicator means. These pH values were compared with the device pH after immersion in distilled water. The difference (ΔpH) was then plotted versus the pH of the buffer used to impregnate the particular device. The results are shown in FIG. 1.

As can be seen from FIG. 1, substantial differences in ΔpH are evident at differing urine specific gravities. The data also shows that these differences do not become discernibly evident until a buffer capable of providing a pH in excess of about 5.5 was employed. Moreover, the differences become more pronounced as the buffer pH increases.

Example II—Control Experiment (PSS)

Figure 2:
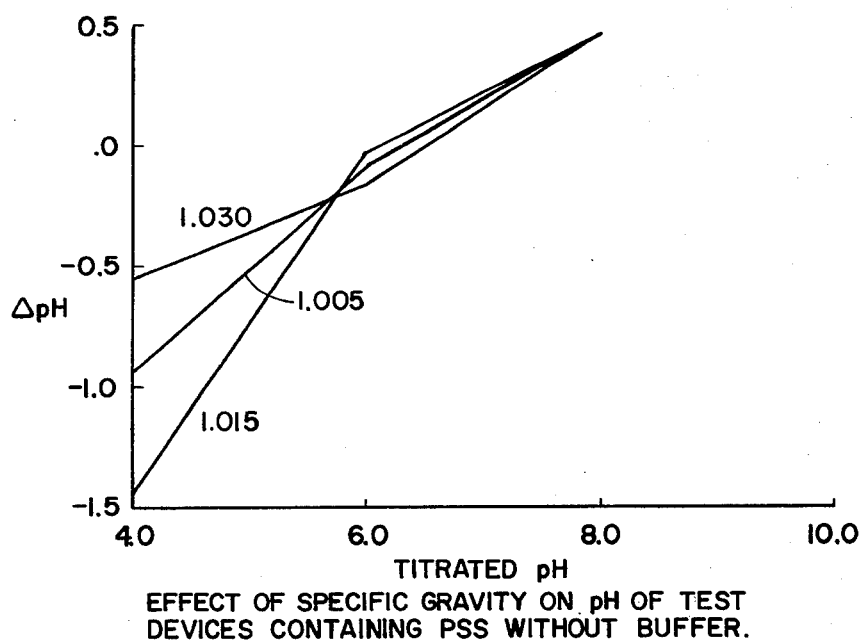

An experiment was performed in which the effect of the buffer in the presently claimed composition was studied. Specifically, strips were prepared as in Example 1 except no buffers were employed. Instead, a 2% solution of PSS in distilled water was titrated to pH's of 4, 6 and 8, respectively, using 1 N NaOH. When a pH of 4.0 was reached in the titration, an aliquot was used to impregnate a piece of Eaton and Dikeman 204 filter paper. At pH 6.0 another piece of filter paper was impregnated. Similarly, a third piece was wetted at pH 8.0. Upon drying, the buffer-free strips were tested as in Example I. The data is presented graphically in FIG. 2.

The graph shows the buffer-free strips to be useless for specific gravity determination. The only observable separation, i.e., significant $\Delta$pH difference with specific gravity, occurred with strips from the pH 4.0 solution. However there is no discernible order to these values, 1.005 producing a $\Delta$pH intermediate to 1.030 and 1.015. Clearly, the presence of a buffer is crucial to obtaining reliable results such as those depicted in FIG. 1.

Example III—The Devices Utilizing Poly(vinylsulfuric acid)

Strips were prepared exactly as in Example I except that poly(vinylsulfuric acid) (hereafter PVS) was substituted for PSS. The three buffered solutions contained the same concentrations of ingredients set forth in Example I and the PVS was present in each at 2% (grams per 100 ml).

Figure 3:
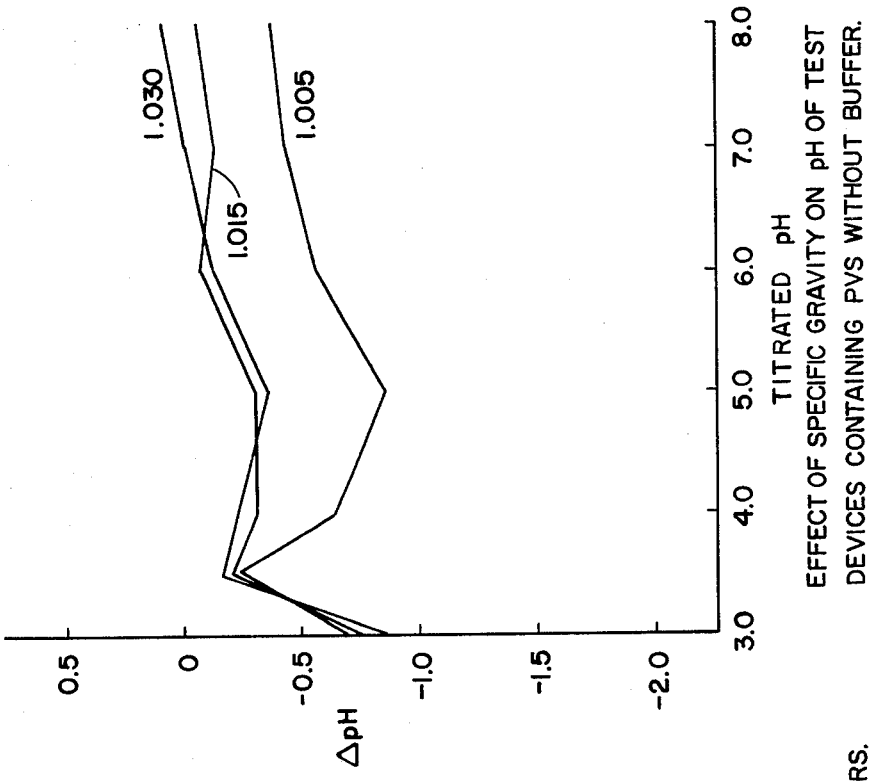

The performance of these strips in differentiating between various urine specific gravities was determined using the same technique as in Example I, and the data is represented graphically in FIG. 3. As with PSS with buffers, strips made with the same buffers, but with PVS as the polyelectrolyte, demonstrated excellent differentiation of different specific gravity levels using buffers capable of providing a pH in excess of about 5.5. Moreover, the resolution of these levels became even more pronounced as the buffer pH increased.

Example IV—Control Experiment (PVS)

Strips were prepared exactly as in Example II except that PVS was substituted for PSS. The procedure was identical in every other respect. These were then compared with the strips of Example III in order to demonstrate the criticality of the buffer to the present invention. The procedure for testing was identical to that of Example I.

Figure 4:
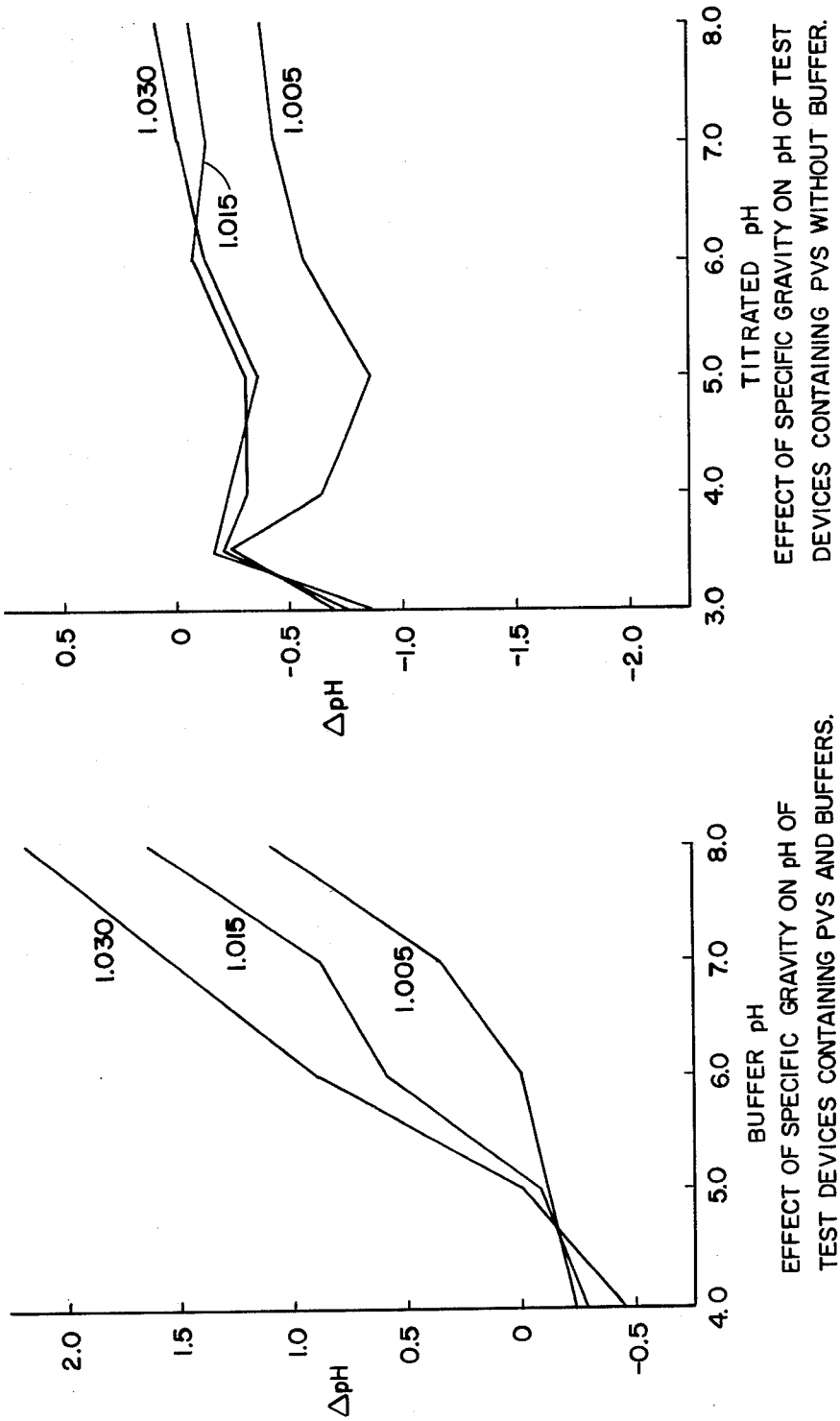

The results of the experiment are represented graphically in FIG. 4 wherein the change in pH ($\Delta$pH) effected by urine specific gravity is plotted versus the pH to which the PVS solution was titrated. The data shows that specific gravity did not correlate to $\Delta$pH, and that therefore the strips were ineffective in gauging specific gravity.

Example V—Test Devices Utilizing Poly(vinylbenzyl ammonium chloride)

Experiments were conducted in order to study the utility of the strongly basic polyelectrolyte, poly(vinylbenzylammonium chloride) (hereafter PVB), in the presently claimed composition. The performance of devices prepared from solutions of the composition was then observed with urine samples of varying specific gravities.

The devices were prepared by dipping strips of Eaton and Dikeman 204 filter paper in solutions of PVB in various buffer solutions. Each solution contained 2% (grams per 100 ml) of PVB. The three buffer solutions used were 0.05 M phosphate (pH 6.0), 0.05 M tris(hydroxymethyl)aminomethane (pH 8.0) and 0.05 M NaHCO$_3$ (pH 10.0). The impregnated strips were then dried and tested in the same manner as in Example I. The data is presented graphically in FIG. 5.

The data shows that specific gravity determination, as a function of pH change in the impregnated paper, is excellent. Moreover, greater differentiation between specific gravity levels was facilitated by greater buffer pH.

Example VI—Control Experiment (PVB)

Control devices comprising filter paper incorporated with PVB, but without buffer, were prepared as in Example II. These were then tested as in Example II to compare their efficacy in determining urine specific gravity.

A 2% solution of PVB in distilled water was prepared. Aliquots of this solution were titrated with 1 N NaOH to pH's of 6.0, 8.0 and 10.0. These three solutions correspond to the pH's of the buffer solution of Example V. Separate strips of Eaton and Dikeman 204 filter paper were immersed in these solutions, respectively, and dried. Upon testing these impregnated strips as in Example II, the data plotted graphically in FIG. 6 was obtained.

Figures 5, 6:
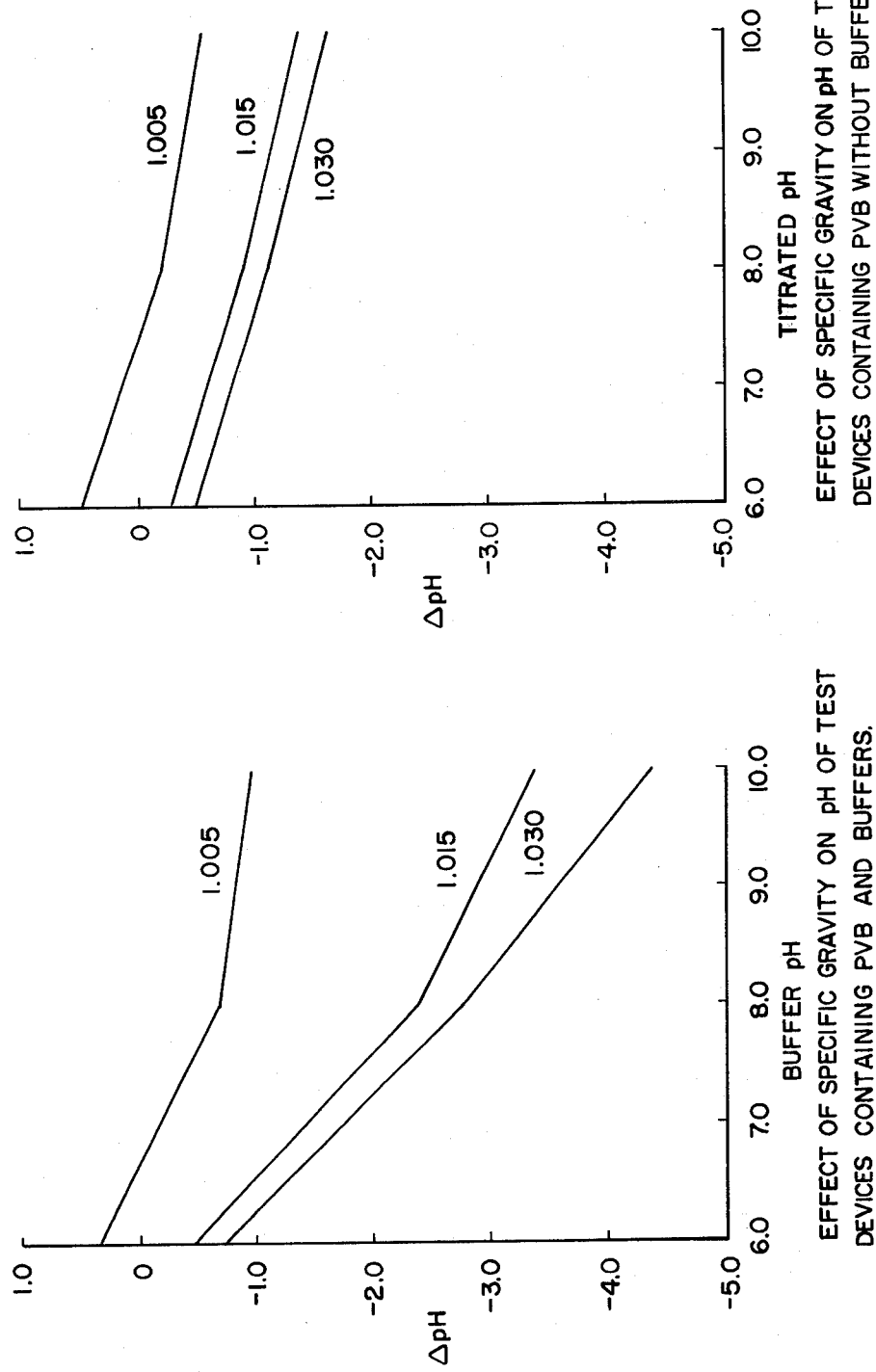

When the data plotted in FIG. 6 is compared with that of FIG. 5, it becomes evident that the buffer is a critical ingredient for useful specific gravity level differentiation.

Examples VII–XIII—Test Devices Utilizing Chromogenic pH Indicators

A series of laboratory experiments was performed to ascertain various pH indicator means compatible with the present concepts. Accordingly, test devices were prepared utilizing chromogenic compounds which undergo color changes in response to changes in the pH of an aqueous system.

The devices were prepared by impregnating strips of filter paper (Eaton and Dikeman 204) with a first dip solution and a second dip solution. The first dip comprised a 0.05 M NaH$_2$PO$_4$ aqueous solution of either PSS or PVB, which had been titrated with NaOH to a pH in the range of 5–8, the specific pH approximating that where the particular chromogen is most responsive. Following the first dip, the paper was dried in an air oven at about 55° C. for about 12 to 15 minutes.

The dried paper was then immersed in the second dip which comprised a chromogenic indicator dissolved in methanol. The twice-dipped paper was then dried as above for about two minutes. Next the paper was mounted onto a sheet of polystyrene backing material using a double faced adhesive tape known as Double Stick (available from 3M Company). Following this lamination step, the composite was cut to provide an elongated polystyrene strip having the impregnated paper portion at one end, the other end serving as a handle.

The polyelectrolyte and chromogen components used for the respective test devices are set forth in the following Table. Also specified are the concentrations of these components used in the respective dip solutions, the pH range of the chromogen, the pH of the first dip after titration with NaOH, and the medium in which the respective devices were tested.

In each case of testing, whether the medium was urine or simple saline (NaCl solution), significant color change was detected between various specific gravity levels, thereby enabling semi-quantitative specific gravity measurement.

TABLE

| Example No. | First Dip Polyelectrolyte | First Dip Concentration (g/dl) | Titrated pH | Second Dip Chromogen & pH range | Second Dip Concentration (mg/dl) | Medium Tested |
| --- | --- | --- | --- | --- | --- | --- |
| VII | PSS | 1.5 | 7.7 | Bromthymol Blue (6.0–7.6) | 118 | Urine and Saline |
| VIII | PVS | 10 | 7.0–7.3 | SAME | SAME | Saline |
| IX | PSS | 1.5 | 6.1–6.7 | Bromcresol Purple (5.2–6.8) | 69.2 | Urine and Saline |
| X | PVS | 10 | 6.1 | SAME | SAME | Saline |
| XI | PSS | 1.5 | 7.7 | Phenol Red (6.8–8.2) | Saturated (<81.2) | Saline |
| XII | PSS | 1.5 | 7.7 | Neutral Red (6.8–8.0) | Saturated (<126) | Saline |
| XIII | PSS | 1.5 | 7.0 | Alizarin (5.6–7.2) | Saturated (<89.6) | Saline |

What is claimed is:

1. A composition capable of producing a detectable response indicative of the specific gravity of a liquid test sample, said composition comprising:
a strongly acidic or strongly basic polyelectrolyte polymer,
a buffer substance capable of providing a pH of at least about 5.5, and
a pH indicator compound.

2. The composition of claim 1 wherein said polyelectrolyte is poly(styrene sulfonic acid), poly(vinyl sulfuric acid), or poly(vinylbenzylammonium chloride).

3. The composition of claim 1, wherein said polyelectrolyte is poly(styrene sulfonic acid).

4. The composition of claims 1, 2 or 3 wherein said buffer substance is citrate, phosphate, glycylglycine or bicarbonate.

5. The composition of claim 4 wherein said buffer substance is phosphate.

6. The composition of claims 1, 2 or 3 wherein said pH indicator compound is bromthymol blue or bromcresol purple.

7. The composition of claim 4 wherein said pH indicator compound is bromthymol blue or bromcresol purple.

8. The composition of claims 1, 2 or 3 wherein said pH indicator compound is bromthymol blue.

9. The composition of claim 4 wherein said pH indicator compound is bromthymol blue.

10. A composition capable of producing a detectable response indicative of the specific gravity of a liquid test sample, said composition comprising poly(styrene sulfonic acid), phosphate, and bromthymol blue.

11. A test device capable of producing a detectable response indicative of the specific gravity of a liquid test sample, the device comprising a carrier matrix incorporated with
a strongly acidic or strongly basic polyelectrolyte polymer,
a buffer substance capable of providing a pH of at least 5.5, and
a pH indicator means.

12. The device of claim 11 wherein said polyelectrolyte polymer is poly(styrene sulfonic acid), poly(vinyl sulfuric acid), or poly(vinylbenzylammonium chloride).

13. The device of claim 11 wherein said polyelectrolyte polymer is poly(styrene sulfonic acid).

14. The device of claim 11 wherein said buffer substance is citrate, phosphate, glycylglycine or bicarbonate.

15. The test device of claim 11 wherein said buffer substance is phosphate.

16. The device of claim 11 wherein said pH indicator means is bromthymol blue or bromcresol purple.

17. The device of claim 11 wherein said buffer substance is citrate, phosphate, glycylglycine or bicarbonate, and said pH indicator means is bromthymol blue or bromcresol purple.

18. The device of one of claims 12 or 13 wherein said pH indicator means is bromthymol blue.

19. The device of claim 11 wherein said buffer substance is citrate, phosphate, glycylglycine or bicarbonate, and said pH indicator means is bromthymol blue.

20. The device of claim 11 wherein said polyelectrolyte polymer is poly(styrene sulfonic acid), said buffer substance is phosphate, and said pH indicator means is bromthymol blue.

21. A method for determining the specific gravity of a liquid test sample, said method comprising contacting the liquid test sample with the device of one of claims 11–17, 19 and 20 and observing said detectable response.

22. A method for determining the specific gravity of a liquid test sample, said method comprising contacting the liquid test sample with the device of claim 18, and observing said detectable response.

* * * * *